(12) United States Patent
Burchfield et al.

(10) Patent No.: US 8,754,366 B2
(45) Date of Patent: Jun. 17, 2014

(54) TANDEM DIFFERENTIAL MOBILITY ION MOBILITY SPECTROMETER FOR CHEMICAL VAPOR DETECTION

(75) Inventors: David E. Burchfield, Rancho Cucamonga, CA (US); H. William Niu, Rowland Heights, CA (US); Richard A. Heppner, Claremont, CA (US)

(73) Assignee: Hamilton Sundstrand Corporation, Rockford, IL (US)

( * ) Notice: Subject to any disclaimer, the term of this patent is extended or adjusted under 35 U.S.C. 154(b) by 0 days.

(21) Appl. No.: 11/033,205

(22) Filed: Jan. 11, 2005

(65) Prior Publication Data
US 2010/0001182 A1 Jan. 7, 2010

(51) Int. Cl.
*H01J 49/00* (2006.01)

(52) U.S. Cl.
USPC .......................... 250/287; 250/283; 250/288

(58) Field of Classification Search
CPC .......... H01J 49/00; B01D 59/44; G01N 27/64
USPC ........................................................ 250/287
See application file for complete search history.

(56) References Cited

U.S. PATENT DOCUMENTS

| | | | |
|---|---|---|---|
| 5,245,192 A | 9/1993 | Houseman | |
| 5,587,581 A | 12/1996 | Stroosnyder | |
| 5,789,745 A | 8/1998 | Martin et al. | |
| 5,968,837 A | 10/1999 | Doring et al. | |
| 6,011,258 A | 1/2000 | Baumbach et al. | |
| 6,442,997 B1 | 9/2002 | Megerle et al. | |
| 6,504,149 B2 | 1/2003 | Guevremont et al. | |
| 6,610,977 B2 | 8/2003 | Megerle | |
| 6,621,077 B1 | 9/2003 | Guevremont et al. | |
| 6,627,878 B1 * | 9/2003 | Machlinski et al. | 250/287 |
| 6,630,663 B2 | 10/2003 | Murphy et al. | |
| 6,639,212 B1 | 10/2003 | Guevremont et al. | |
| 6,653,627 B2 | 11/2003 | Guevremont et al. | |
| 6,690,004 B2 * | 2/2004 | Miller et al. | 250/286 |
| 6,703,609 B2 | 3/2004 | Guevremont et al. | |
| 7,170,052 B2 * | 1/2007 | Furutani et al. | 250/287 |
| 7,227,134 B2 * | 6/2007 | Miller et al. | 250/288 |

FOREIGN PATENT DOCUMENTS

| | | |
|---|---|---|
| JP | 5029099 | 3/1975 |
| JP | 10288602 | 10/1998 |
| WO | 02071053 | 9/2002 |

OTHER PUBLICATIONS

English translation of Japanese Office Action mailed Jun. 22, 2010, JP Application No. 2007-556140.

(Continued)

*Primary Examiner* — Phillip A Johnston
(74) *Attorney, Agent, or Firm* — Carlson, Gaskey & Olds, P.C.

(57) ABSTRACT

A DMS-IMS chemical sensing system employs two ion-separation technologies in tandem to extract signals of specific chemicals from the glut of signals present. The sensing system generally includes an atmospheric pressure ion generation system, a Differential Mobility (DMS) system, a time-of-flight IMS (TOF-IMS) system, and an ion detector system. The DMS extracts a narrow range of trace chemicals from an environmental sample for subsequent analysis, and a TOF-IMS then analyzes the resulting narrow range of isolated chemicals, allowing compound-specific detection thresholds at sub-ppb concentrations.

7 Claims, 3 Drawing Sheets

(56) References Cited

OTHER PUBLICATIONS

Makela J M et al: "Mobility distribution of acetone cluster ions" Journal of Aerosol Science Mar. 1996, vol. 27, No. 2, Mar. 1996, pp. 175-190, XP7913232.

Turner R B et al: "Hand-Held Ion Mobility Spectrometers" TRAC. Trends in Analytical Chemistry, vol. 13, No. 7, Aug. 1, 1994, pp. 275-280, XP000457608.

Guevremont R et al.: "Ion Trapping at Atmospheric Pressure (760 Torr) and Room Temperature with a High-field Asymmetric Waveform Ion Mobility Spectrometer", International Journal of Mass Spectrometry, vol. 193, No. 1, Oct. 28, 1999, pp. 45-56, XP004365756.

PCT International Search Report and Written Opinion mailed Jun. 8, 2010, PCT/US2006/000889.

* cited by examiner

| Chemical Agents | PEL (IDLH) in ppm (a) | DMS Response PEL | DMS Response 0.1xIDLH |
|---|---|---|---|
| GA | 0.0001 (0.2) | Y+/- | Y+/- |
| GB | 0.0001 (0.2) | Y+/- | Y+/- |
| GD | 0.00003 (0.06) | Y+/- | Y+/- |
| GF | 0.00003 (0.06) | Y+/- | Y+/- |
| VX | 0.00001 (0.02) | Y (b)+/- | Y+/- |
| HD | 0.005 | Y+/- | Y+/- |
| HN | 0.004 | Y+/- | Y+/- |
| HL | 0.004 | Y+/- | Y+/- |
| L | 0.004 | Y | Y |
| AC (see HC N, below) | 4.7st (50) | Y | Y |
| CK | 0.3ceil | Y | Y |
| CG (see phosgene) | 0.1 (2) | Y | Y |
| DP | 0.1 (2 lc50) | Y | Y |
| Toxic Industrial Chemicals (TICs) | | | |
| Allyl alcohol | 2 (150) | Y | Y |
| Acrolein | 0.1 (5) | Y | Y |
| Acrylonitrile | 1 (500) | Y | Y |
| Ammonia | 25 (500) | Y | Y |
| Arsine | 0.05 (6) | Y | Y |
| Chlorine | 0.5 (30) | Y | Y |
| Diborane | 0.1 (40) | Prob. | Prob. |
| Ethyl Oxide | 1 (800) | Y | Y |
| Formaldehyde | 1 (30) | Y | Y |
| Hydrogen Bromide | 3 ceil (50) | Y | Y |
| Hydrogen Chloride | 5 ceil (100) | Y- | Y- |
| Hydrogen Cyanide | 4.7st (50) | Y | Y |
| Hydrogen Fluoride | 3 (30) | Y- | Y- |
| Hydrogen Selenide | 0.05 (2) | Y | Y |
| Hydrogen Sulfide | 10 (30) | Y | Y |
| Methyl Hydrazine | 0.2ceil (50) | Y | Y |
| Hydrazine | 0.1 (80) | Y | Y |
| Methyl isocyanate | 0.02 (20) | Y | Y |
| Methyl mercaptan | 0.5 (400) | Y | Y |
| Nitrogen Dioxide | 1st (50) | Prob. | Prob. |
| Nitric Acid | 2 (100) | Prob. | Prob. |
| Nitric Acid (fuming) | | Prob. | Prob. |
| Phosgene (CG, above) | 0.1 (2) | Y | Y |
| Phosphine | 0.3 (200) | Y | Y |
| Sulfuric Acid | 1 mg/m³ (15 mg/m³) | No | No |
| Sulfur oxides | 2 (100) | No | No |
| Toluene 2,4-diisocyanate | 0.005 (10) | Y | Y |
| a. Personal Exposure Limit in parts per million, per NIOSH Guide to Chemical Hazards. Unless otherwise noted, the PEL is an 8 hour time weighted average exposure limit; (ceiling) is a short term exposure do-not-exceed, and (st) typically defines a 15 minute exposure time weighted average limit. b. Requires preconcentration to meet PEL detection threshold. | | | |

Fig-5

TANDEM DIFFERENTIAL MOBILITY ION MOBILITY SPECTROMETER FOR CHEMICAL VAPOR DETECTION

BACKGROUND OF THE INVENTION

The present invention relates to a chemical sensing system, and more particularly to a sensing system that utilizes two ion-separation technologies in tandem to detect specific chemicals in the presence of common environmental chemical backgrounds.

Sensing to identify and quantitate specific chemicals is of interest for a variety of purposes, including assuring human safety in environments that may contain threats from Toxic Industrial Chemicals (TICs) or Chemical Warfare Agents (CWAs), and in industrial process control. Chemical sensing for environmental monitoring must be compatible with safety requirements, as specifically promulgated by OSHA and other government organizations through time-weighted average Permissible Exposure Limits (PELs). These standards are also broadly applied to potential chemical threats. Many TICs, including pesticides, acid vapors, and carcinogens, and the CWAs have PELs that range from part per million (ppm) and part per billion (ppb) levels to part-per-trillion (ppt) levels in air. At those low concentrations the air we breathe can have hundreds of other chemicals (scents, simple hydrocarbons, and other non-toxic vapors) in addition to near percent loads of water and carbon dioxide. Similarly, industrial process streams may have the chemicals to be monitored embedded in complex mixtures. Accurately and sensitively detecting the compounds of interest in the presence of complex and variable chemical backgrounds has historically required advanced laboratory analytical separations and complex instrumentation, such as gas chromatograph-mass spectrometry (GC-MS). GC-MS is a tandem or "hyphenated" analytical technique that represents a laboratory level standard for chemical mixture analysis, where the resolving power of two "orthogonal" measurement techniques that respond to different physical/chemical properties is used to extract signals from a complex sample matrix.

There is a looming possibility that civilians and first responders may be exposed to environments involving hazardous chemicals including CWAs. Low-cost portable and fixed site sensors providing reliable detection of TICs and CWAs at ppb and sub-ppb levels are required to provide rapid, on-site characterization and warning of the threat in the event of an attack or incident. No portable sensor technology exists that can detect specified lists of TICs and CWAs at the sub-ppb levels in real time and with acceptable false-alarm rates in the presence of common environmental chemical backgrounds.

Variations of Ion-Mobility Spectrometry (IMS) have been utilized for chemical vapor detection. The variants include Time-of-Flight IMS (TOF-IMS), Radio Frequency IMS (RFIMS), and a technique known either as Field Asymmetric IMS (FAIMS) or Differential Mobility Spectrometry (DMS). As with TOF-IMS, the FAIMS and DMS variants are highly sensitive with moderate specificity. However, both TOF-IMS and DMS are increasingly subject to false detection as sensor gain is increased and sub-ppm limits of detection are pursued, this due to the more complex nature of samples at ppb and ppt levels. While DMS technology has the sensitivity to approach PEL level detection of CWAs without preconcentration, resolution becomes a limiting factor in the presence of trace environmental chemical backgrounds.

Accordingly, it is desirable to provide a chemical sensing system that detects specified lists of TICs and CWAs at the sub-ppb levels in real time and in the presence of common environmental chemical backgrounds.

SUMMARY OF THE INVENTION

The sensor system according to the present invention includes a tandem DMS-IMS chemical sensing system that employs two ion-separation technologies in tandem to extract signals characteristic of specific chemicals in the presence of common environmental chemical backgrounds. The sensing system generally includes an ion generation system, a DMS system, a TOF-IMS system, and an ion detector system.

The DMS system extracts a narrow range of trace chemicals from an environmental sample for subsequent analysis, and one or more TOF-IMS detectors then analyze the resulting narrow range of isolated chemicals. The resulting 'hyphenated technique' of DMS-IMS allows compound-specific detection thresholds of sub-ppb concentrations with a sensor that is not significantly more complex than an IMS alone.

The combination of the differential mobility of the DMS and ion mobility of the IMS provides significant resolving power. The physical-chemical principles upon which the resolving properties of these devices are based differ sufficiently that their ion separations are highly orthogonal. Under this condition, the effective resolving power of the detection system approximates the product of the resolving power of each system alone. This allows the system to detect chemicals in air at ultra-trace levels while minimizing false positive detections. Moreover, the tandem sensor technologies upon which this higher performance is based are still particularly well suited to miniaturization, low power implementation and relatively low manufacturing cost.

The present invention therefore provides a chemical sensing system that detects specified lists of TICs and CWAs at sub-ppb levels in real time and in the presence of common environmental chemical backgrounds.

BRIEF DESCRIPTION OF THE DRAWINGS

The various features and advantages of this invention will become apparent to those skilled in the art from the following detailed description of the currently preferred embodiment. The drawings that accompany the detailed description can be briefly described as follows:

FIG. 5 is a table illustrating various CWAs and TICs that a tandem DMS-IMS analyzer may be programmed to detect.

DETAILED DESCRIPTION OF THE PREFERRED EMBODIMENT

Figure 1:
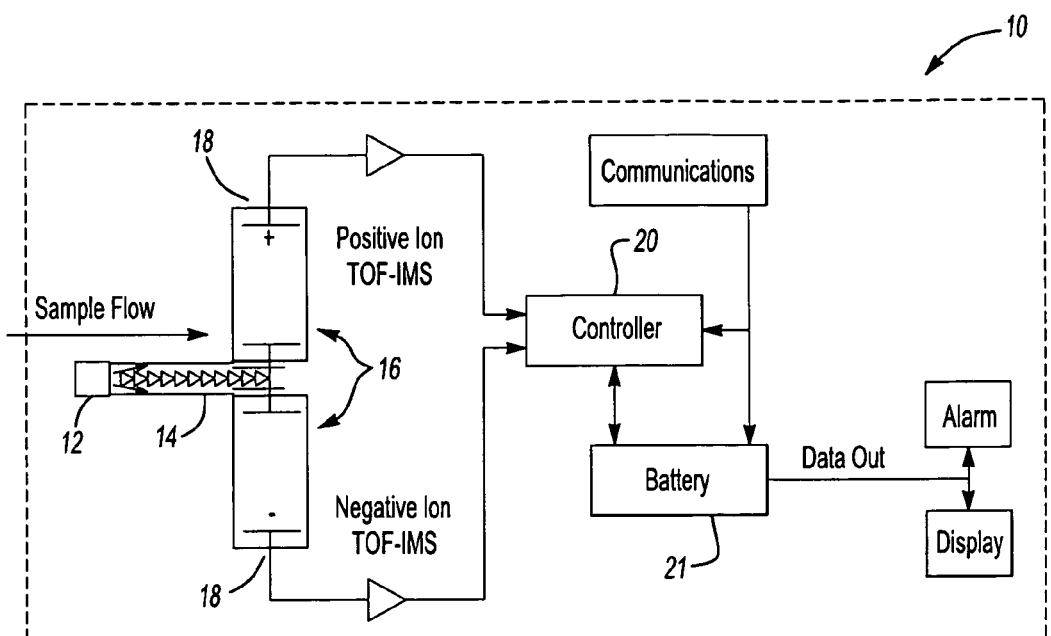
FIG. 1 is a block diagram of a chemical sensing system according to the present invention.

FIG. 1 illustrates a general schematic view of a chemical sensing system 10. The sensing system 10 generally includes an atmospheric pressure ionization (API) system 12, a Differential Mobility Spectrometry (DMS) system 14, and a Time-of-Flight Ion Mobility Spectrometry (TOF-IMS) system 16. The TOF-IMS system 16 includes an ion detector system 18, which communicates with a controller 20 (also schematically illustrated in FIG. 2). Instrument control and analysis functions to detect specified lists of TICs and CWAs are programmed into the controller 20 and are reconfigurable via a communication system 21. The communication system 21 could perhaps be via serial or parallel interface, could be established via a Wi-Fi network, or could be based on a self-configuring RF network, with software for remote commanding and data analysis layered onto the selected communications link.

Generally, the API system 12 rejects simple hydrocarbon interferences while efficiently ionizing target molecules. From the API system 12 ions are communicated to the DMS system 14 under a gas flow. The DMS system 14 is adjusted or "tuned" to allow a narrow range of target ions such as CWAs and TICs to pass through, neutralizing most of the background ions created in the API source. From the DMS system 14, the target ions are communicated into the TOF-IMS system 16 and the detector system 18, which measures the ion mobility spectra of all species present for comparison to the TOF-IMS spectra of known CWAs and TICs.

Figure 3:
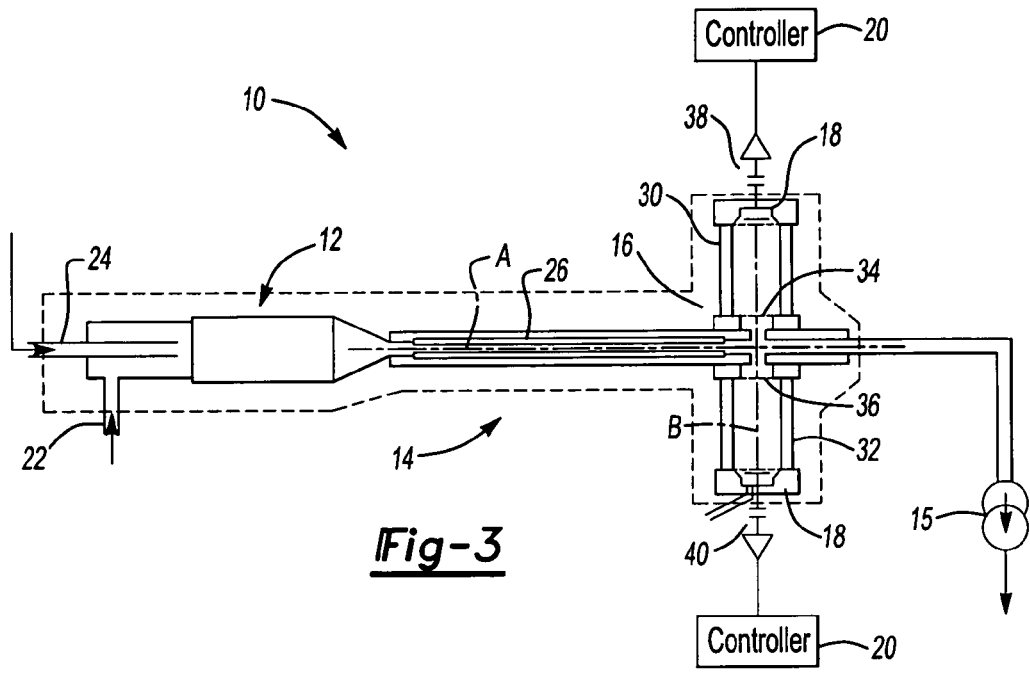
FIG. 3 is a general schematic view of a chemical sensing system according to the present invention.

Referring to FIG. 3, the system 10 employs both the DMS system 14 and the TOF-IMS system 16 in tandem to extract signals of specific chemicals including specified lists of TICs and CWAs in the presence of common environmental chemical backgrounds. Since differential mobility is largely a function of chemical type with highest resolution for low-mass ions, and time-of-flight ion mobility is fundamentally dependent on molecular weight and ion cross-section, the result is a highly sensitive, highly specific sensing system.

The API system 12 receives filtered air through a filtered air conduit 22 and sample air through a sample air conduit 24. Preferably, the API system 12 includes an atmospheric pressure ionization source including a photoionization source, corona discharge source, beta decay source, or alpha decay source, in which air and/or chemical vapors ionize as they enter from the sample air conduit 24. Airflow through the chemical sensing system 10 is effected by a sample pump 15 that draws the sample air into a recirculating, scrubbed flow in which humidity and organic vapor concentrations are preferably maintained at relatively low level.

Figure 4:
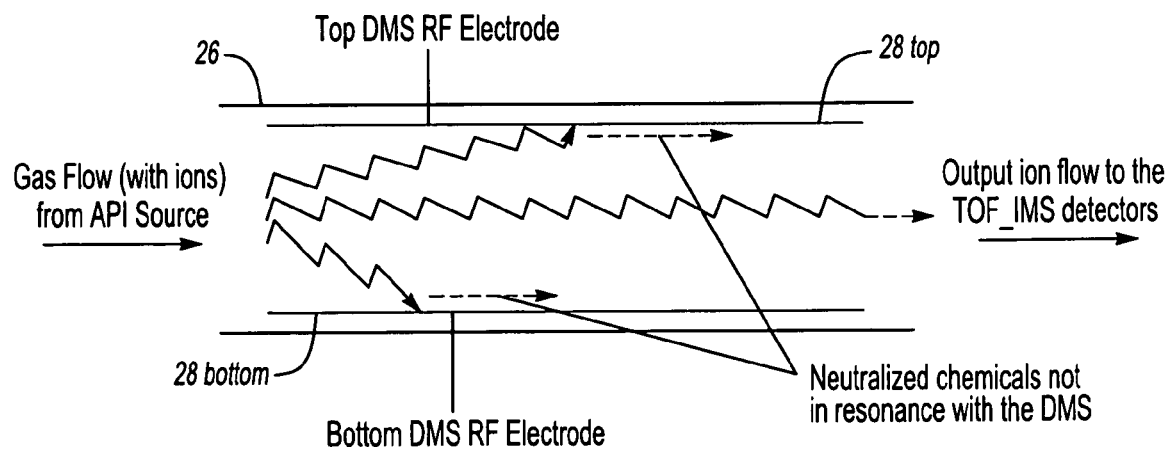
FIG. 4 is a schematic view of a Differential Mobility Spectrometer drift cell and representational ion traces passing therethrough.

The DMS system 14 includes a DMS drift cell 26, a planar structure with two electrodes that defines an axis A. Materials that obtain a charge in the ionization source 12 at the front of the DMS drift cell are pushed between the pair of electrodes 28 (FIG. 4). Voltages are applied to the electrodes 28 to effect an asymmetrically-oscillated electric field perpendicular to the ion path A. The controller 20 applies a brief high electric field followed by a lower field of opposite polarity for a longer time, such that the time-weighted applied field is nearly zero. In the time required for an ion to transit the DMS drift cell 26 to the TOF-IMS system 16, about 1 millisecond, the RF cycle is repeated approximately 1000 times.

As the bulk flow of ions transit the DMS drift cell 26, ions are forced by the oscillating field into a zig-zag or saw-tooth path, here greatly exaggerated (FIG. 4). Ions with the same mobility or effective molecular cross-section under high and low-field conditions will travel a zig-zag path averaging down the middle of the DMS drift cell. Most molecular ions, and notably many CWAs and TICs, do not have equal high- and low-field mobilities. This happens when the molecule deforms in high fields, changing its cross-section. It also results when the molecular ion has sufficient affinity for clustering with water molecules in low fields, but collisionally declusters in high fields. For such molecules, the different voltages interact with these properties to cause the ions to drift toward either the upper electrode plate 28$t$ or the bottom electrode plate 28$b$, a little with each cycle. Over the many cycles the ions undergo, any unbalanced up or down net movement eventually forces the ions into contact with the electrode plates 28$t$, 28$b$ where they are neutralized.

At any one time, most ions entering the DMS drift cell 26 impact upon the plates 28, are neutralized, and then are carried out of the system 10 as neutral molecules. Only those ions that successfully transit the length of the DMS drift cell without contacting the electrodes 28, i.e. those ions in tune with the applied electric field, are analyzed and detected by the TOF-IMS system 16 detectors. In practice, offset voltages, also known as compensation voltages, are added to the RF voltages, biasing the electric fields such that different ions are selected to pass through the DMS drift cell, thereby scanning the range of differential mobilities. The compensation voltage at which an ion is transmitted through the DMS is a measure of that ion's differential mobility.

The DMS system 14 provides continuously scanned and/or step-scanned functions to allow passage of specific ions using a combination of RF field amplitude and DC compensation voltage to modify the DMS drift cell 26 transmission. Chemical vapors or dopants may be added to the sample air in the drift cell to complex with target ions in the DMS drift cell, increasing target ion differential mobility, or to quench the formation of some interfering ions, depending on the chemicals to be detected.

For example only, a nerve agent like sarin has a phosphorous-oxygen core (P=O) that, when protonated, has an affinity for water. In humid air, the ion sarin forms in a DMS is Sarin.H+.nH$_2$O, with the number (n) of associated water molecules dependent on temperature and humidity. Under very high fields, the ion is pulled so rapidly through the air that its collisions with air molecules decluster most of the water, leaving Sarin.H+0.1H$_2$O, with a smaller collisional cross-section. When the field reverses and drops in amplitude, the ion is allowed to recluster with water molecules from the air around it and gets bigger again. The net effect is that the ion is smaller under the high-field portion of the RF cycle, larger under the low-field portion, and this size difference leads to a tendency to drift upward as the ion travels its sawtooth path down the DMS cell.

Thus, when the DMS system 14 is tuned to measure sarin, this upward drift must be countered. An offset voltage CV is applied to the electrode plates 28*t*, 28*b* so that as the ions are pulled up by the sawtooth, they are electrostatically driven back toward the center of the DMS. This reduces the efficiency of the 'up' sawtooth, and increases the efficiency of the down sawtooth, allowing any sarin present, and any other ions of similar differential mobility to transit down the DMS system 14. Under this condition, ions of 0 differential mobility that were transiting the system under a CV of 0 volts are now dragged into the bottom electrode plate 28*b*.

Only those ions that transit the DMS system 14 without contacting the upper or lower electrodes 28*t* and 28*b* are available to the TOF-IMS system 16 for analysis. Target species are caused to transit the DMS system 14 by setting the DMS system electrodes to specific compensation voltages, and the TOF-IMS system detects any target species present by measuring the signals associated with ions transiting the DMS system 14.

The TOF-IMS system 16 includes one or more IMS drift cells arranged to detect ions passed by the DMS system 14. FIG. 2 illustrates one possible configuration, showing both a positively-biased TOF-IMS drift cell 30 and a negatively-biased IMS drift cell 32 coupled to the DMS drift cell 26 to simultaneously analyze both the positive and negative ions that are in tune with the DMS applied electric field. When two TOF-IMS drift cells 30 and 32 are used, they are preferably arranged to define an ion flow axis B transverse to axis A. Other geometries can be conceived for interfacing TOF-IMS drift cells to a DMS system, and are part of this invention.

The positive and negative ions in the DMS system exhaust are pulled toward a pair of ion gate electrodes 34 and 36 under an applied electric field. Once at these electrodes, the ions are gated into one of two TOF-IMS drift cells, 30 for the positive ions and 32 for negative ions. The pulses of ions gated into each TOF-IMS cell are drawn down the length of the cells under an applied electric field, while the controller 20 measures the number of microseconds the ions take to get from the gate electrode at one end to the ion detector at the other end. The controller 20 drives the ion gate electrode 34, 36 modulation patterns (FIG. 2).

Figure 2:
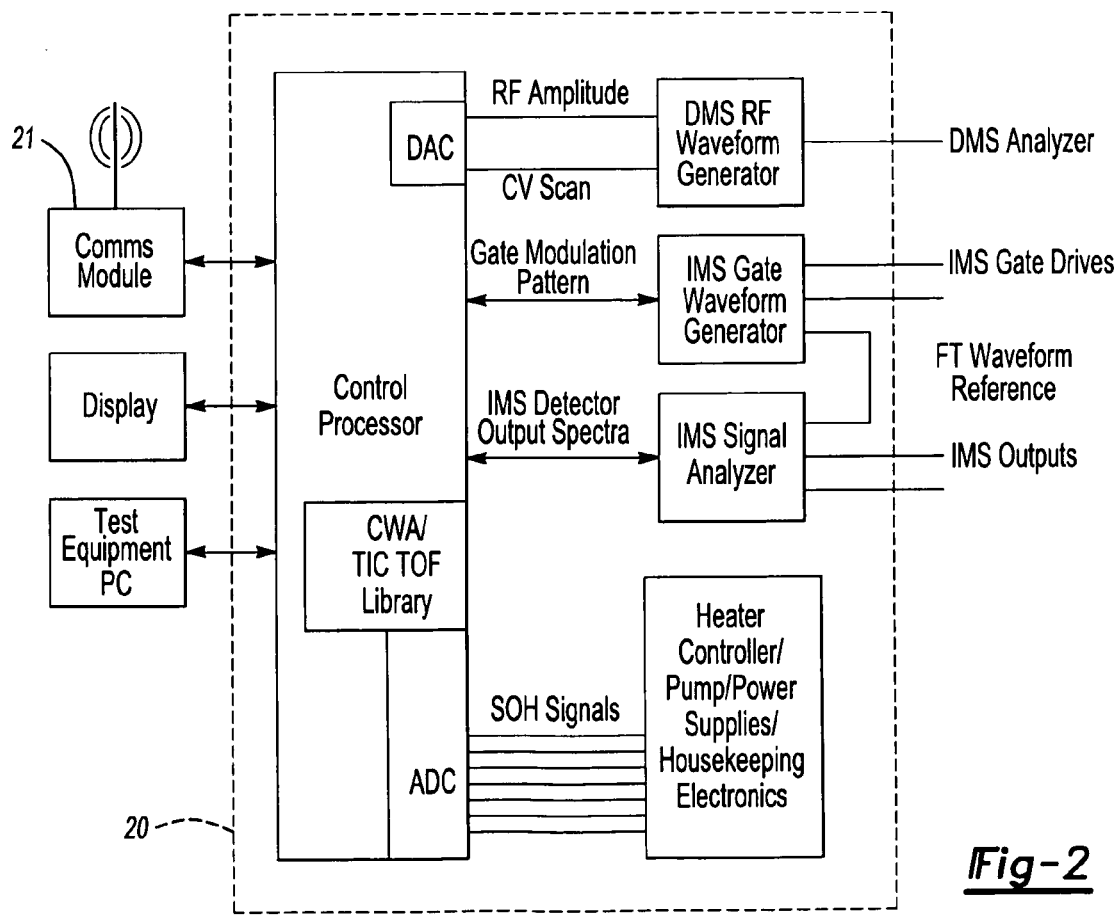
FIG. 2 is a block diagram of a controller for a chemical sensing system.

Each TOF-IMS drift cell 30, 32, is terminated with an ion detector 38, 40, which communicates with the controller 20 (FIG. 2). Each ion detector 38, 40 is preferably a Faraday collector. Other detectors such as a charge-coupled Faraday collector, delta-doped silicon charge coupled device, or ion multiplier that is sensitive to the ions transmitted down the TOF-IMS drift cells 30, 32 may alternatively or additionally be utilized.

Determination of drift time by the TOF-IMS system 16 is effected by time-of-flight detection, measuring signals as a function of delay time following the admittance of ions into the drift cells 30, 32. Ion drift times may be determined using single gate/analyze time-of-flight measurements, or using a gate correlation technique. The measured IMS drift times are then converted to mobility by normalization to drift field, temperature, and cell pressure. A TOF-IMS system 16 sorts the ions by molecular weight and collisional cross-section, obtaining a resolution of approximately one part in 100. The TOF-IMS system 16 also provides simultaneous positive and negative ion detection, providing real-time confirmation of target detection for certain analytes, including nerve and blister agents. Extensive detection libraries of the DMS differential mobilities and time-of-flight IMS mobilities of particular CWAs and TICs are preferably stored within the controller 20 for comparison and identification (FIG. 1).

The combination of the differential mobility of the DMS and ion mobility of the TOF-IMS provides significantly higher resolution than either DMS or TOF-IMS, providing a resolving power approximately equal to the product of each technology alone. This permits the system 10 to detect chemicals in air at ultra trace levels while minimizing false positive detections, using a technology compatible with portable sensors. In short, the DMS-IMS chemical sensing system 10 represents a significant advantage over either technology alone in sensitivity and resolution, and possesses the required characteristics for application to trace chemical detection.

Referring to FIG. 5, detection—indicated by a Y in columns 3 and 4—for CWAs and TICs as provided by the DMS-IMS chemical sensing system 10 is readily achieved. Confirmation is also available in every scan using dual positive and negative ion detection capability for those CWA materials that exhibit dual mode sensitivity (Y+/−).

The foregoing description is exemplary rather than defined by the limitations within. Many modifications and variations of the present invention are possible in light of the above teachings. The preferred embodiments of this invention have been disclosed, however, one of ordinary skill in the art would recognize that certain modifications would come within the scope of this invention. It is, therefore, to be understood that within the scope of the appended claims, the invention may be practiced otherwise than as specifically described. For that reason the following claims should be studied to determine the true scope and content of this invention.

What is claimed is:

1. A chemical sensing system comprising:
an ionization system operable to ionize sample molecules;
a differential mobility cell connected to said ionization system to receive ionized sample molecules therefrom, said differential mobility cell including a plurality of electrodes operable to apply an electric field in said differential mobility cell;
a time-of-flight ion-mobility spectrometry system downstream of said differential mobility cell operable to analyze target ions of said ionized sample molecules to produce a time-resolved spectrum of ions, said time-of-flight ion-mobility spectrometry system including first and second ion mobility drift cells configured to detect, respectively, positive and negative ions from said differential mobility cell,
wherein said positive ions exiting the differential mobility cell are pulled toward a first ion gate electrode and gated into said first ion mobility drift cell, and said negative ions exiting the differential mobility cell are pulled toward a second ion gate electrode and gated into said second ion mobility drift cell; and
a controller in communication with said plurality of electrodes, said controller configured to control said electric field in tune with said target ions of the ionized sample molecules such that said target ions do not become neutralized by contact with an electrode and are permitted to pass through the differential mobility cell to the time-of-flight ion-mobility spectrometry system.

2. The chemical sensing system as recited in claim 1, further comprising a detector system in communication with said time-of-flight ion-mobility spectrometry system.

3. The chemical sensing system as recited in claim 1, further comprising first and second ion detectors at, respectively, the end of each of said first and second ion mobility drift cells.

4. The chemical sensing system as recited in claim 3, wherein each of said first and second ion detectors communicate with said controller.

5. The chemical sensing system as recited in claim 4, wherein said target ions include only CWAs, and TICs.

6. The chemical sensing system as recited in claim 1, wherein said differential mobility cell and said time-of-flight ion-mobility spectrometry system are sized to provide a portable system.

7. The chemical sensing system as recited in claim 1, further comprising a power source to power said differential mobility cell and said time-of-flight ion-mobility spectrometry system, said power source powered by one or more batteries.

* * * * *